(12) United States Patent
Chen et al.

(10) Patent No.: US 9,127,025 B2
(45) Date of Patent: Sep. 8, 2015

(54) ZN$_5$(BTA)$_6$(TDA)$_2$—A ROBUST HIGHLY INTERPENETRATED METAL-ORGANIC FRAMEWORK CONSTRUCTED FROM PENTANUCLEAR CLUSTERS FOR SELECTIVE SORPTION OF GAS MOLECULES

(75) Inventors: Banglin Chen, San Antonio, TX (US); Shengchang Xiang, Fuzhou (CN)

(73) Assignee: The Board of Regents of The University of Texas System, Austin, TX (US)

( * ) Notice: Subject to any disclaimer, the term of this patent is extended or adjusted under 35 U.S.C. 154(b) by 420 days.

(21) Appl. No.: 13/589,746

(22) Filed: Aug. 20, 2012

(65) Prior Publication Data

US 2013/0043407 A1    Feb. 21, 2013

Related U.S. Application Data (60) Provisional application No. 61/575,375, filed on Aug. 19, 2011.

(51) Int. Cl.
*B01J 20/22* (2006.01)
*C07F 3/06* (2006.01)
(Continued)

(52) U.S. Cl.
CPC ............. *C07F 3/06* (2013.01); *B01J 20/226* (2013.01); *B01J 20/28057* (2013.01); *B01J 20/28071* (2013.01); *C01B 3/0015* (2013.01);
(Continued)

(58) Field of Classification Search
CPC ............. G01N 33/0045; G01N 31/22; G01N 33/1813; G01N 21/3103; G01N 33/84; G01N 21/6428; G01N 21/6458; G01N 21/64; G01N 21/6408; G01N 2021/6421; B01D 2253/102; B01D 53/02; B01D 2253/108; B01D 53/0446; B01D 2253/104; B01J 20/32; B01J 53/02; B01J 20/24; B01J 20/26; B01J 20/3242; C01F 3/12; C09B 57/04; C09B 57/10; C09K 11/06; C09K 2211/185
USPC .............. 436/81; 250/459.1; 95/90; 502/401; 548/108
See application file for complete search history.

(56) References Cited

U.S. PATENT DOCUMENTS 7,662,746 B2    2/2010    Yaghi et al.
2006/0252641 A1    11/2006    Yaghi et al.
(Continued)

FOREIGN PATENT DOCUMENTS

JP    2003-342260    12/2003
JP    2004-161675    6/2004
(Continued)

OTHER PUBLICATIONS

Luminescent metal-organic frameworks M.D. Allendorf, C.A. Bauer, R.K. Bhakta, and R.J.T. Houk Chem. Soc. Rev., 2009, 38, 1330-1352.*
(Continued)

*Primary Examiner* — Krishnan S Menon
*Assistant Examiner* — Dwan A Gerido
(74) *Attorney, Agent, or Firm* — Parker Highlander PLLC (57) ABSTRACT

Disclosed herein are highly interpenetrated robust metal-organic frameworks having the repeat unit Zn$_5$(BTA)$_6$(TDA)$_2$, useful for applications such as selective gas storage, selective gas sorption and/or separation, and gas detection.

20 Claims, 7 Drawing Sheets

(51) Int. Cl.
| | |
|---|---|
| G01N 21/64 | (2006.01) |
| B01D 53/02 | (2006.01) |
| B01J 20/28 | (2006.01) |
| C01B 3/00 | (2006.01) |
| C01B 21/04 | (2006.01) |
| C01B 21/24 | (2006.01) |
| C01B 21/36 | (2006.01) |
| C01B 23/00 | (2006.01) |
| G01N 31/22 | (2006.01) |

(52) U.S. Cl.
CPC ............. *C01B21/0472* (2013.01); *C01B 21/24* (2013.01); *C01B 21/36* (2013.01); *C01B 23/0073* (2013.01); *B01D 53/02* (2013.01); *B01D 2253/204* (2013.01); *B01D 2256/245* (2013.01); *B01D 2257/504* (2013.01); *B01D 2257/7022* (2013.01); *C01B 2210/0034* (2013.01); *Y02C 10/08* (2013.01); *Y02E 60/328* (2013.01)

(56) References Cited

U.S. PATENT DOCUMENTS

| | | | |
|---|---|---|---|
| 2007/0248852 A1 | 10/2007 | Mueller et al. | 95/90 |
| 2007/0252641 A1 | 11/2007 | Goodnow et al. | 327/543 |

FOREIGN PATENT DOCUMENTS

| | | |
|---|---|---|
| JP | 2004-305985 | 11/2004 |
| WO | WO 2008/000694 | 1/2008 |

OTHER PUBLICATIONS

A Robust Highly Interpenetrated Metal-Organic Framework Constructed from Pentanuclear Clusters for Selective Sorption of Gas Molecules Inorg. Chem, 2010, 49, 8444-8448 Zhangjing Zhang, Shengchang Xiang, Yu-Sheng Chen, Shengqian Ma, Yongwoo Lee, Thomas Phely-Bobin, and Banglin Chen.*
Babarao, et al., "Storage and separation of CO2 and CH4 in silicalite, C168 schwarzite, and IRMOF-1: a comparative study from Monte Carlo simulation," *Langmuir*, 23:659-66, 2007.
Bai, et al., "The designed assembly of augmented diamond networks from predetermined pentanuclear tetrahedral units," *Agnew. Chem. Int. Ed. Engl.*, 47:5344-7, 2008.
Banerjee, et al., "Control of pore size and functionality in isoreticular zeolitic imidazolate frameworks and their carbon dioxide selective capture properties," *J. Am. Chem. Soc.*, 131:3875-7, 2009.
Bauer, et al., "Influence of connectivity and porosity on ligand-based luminescence in zinc metal-organic framework," *J. Am. Chem. Soc.*, 129:7136-44, 2007.
Bourrelly, et al., "Different adsorption behaviors of methane and carbon dioxide in the isotypic nanoporous metal terephthalates MIL-53 and MIL-47," *J. Am. Chem. Soc.*, 127:13519-21, 2005.
Busker, et al., "Isomer-selective vibrational spectroscopy of benzene-acetylene aggregates: comparison with the structure of the benzene-acetylene cocrystal," *Angew. Chem. Int. Ed. Engl.*, 47:10094-7, 2008.
Britt, et al., "Highly efficient separation of carbon dioxide by a metal-organic framework replete with open metal sites," *PNAS*, 106:20637-40, 2009.
Caskey, et al., "Dramatic tuning of carbon dioxide uptake via metal substitution in a coordination polymer with cylindrical pores," *J. Am. Chem. Soc.*, 130:10870-1, 2008.
Chandler, et al., "Microporous metal-organic frameworks formed in a stepwise manner from luminescent building blocks," *J. Am. Chem. Soc.*, 128:10403-12, 2006.
Chen, et al., "A luminescent microporous metal-organic framework for the recognition and sensing of anions," *J. Am. Chem. Soc.*, 6718-9, 2008.
Chen, et al., "A microporous metal-organic framework for gas-chromatographic separation of alkanes," *Angew. Chem. Int. Ed. Engl.*, 45:1390-3, 2006.
Chen, et al., "A triply interpenetrated microporous metal-organic framework for selective sorption of gas molecules," *Inorg. Chem.*, 46:8490-2, 2007.
Chen, et al., "High H2 adsorption in a microporous metal-organic framework with open metal sites," *Angew. Chem. Int. Ed. Engl.*, 44:4745-9, 2005.
Chen, et al., "Luminescent open metal sites within a metal-organic framework for sensing small molecules," *Adv. Mater.*, 19:1693-6, 2007.
Chen, et al., "Metal-organic frameworks with functional pores for recognition of small molecules," *Acc. Chem. Res.*, 43:1115-24, 2010.
Chen, et al., "Multiroute synthesis of porous anionic frameworks and size-tunable extraframework organic cation-controlled gas sorption properties," *J. Am. Chem. Soc.*, 131:16027-9, 2009.
Chen, et al., "Rationally designed micropores within a metal-organic framework for selective sorption of gas molecules," *Inorg. Chem.*, 46:1233-6, 2007.
Chen, et al., "Selective gas sorption within a dynamic metal-organic framework," *Inorg. Chem.*, 46:9705-9, 2007.
Chen, et al., "Surface interactions and quantum kinetic molecular sieving for H2 and D2 adsorption on a mixed metal-organic framework material," *J. Am. Chem. Soc.*, 130:6411-23, 2008.
Choi and Suh, "Highly selective $CO_2$ capture in flexible 3D coordination polymer networks," *Angew. Chem.*, 121:6997-7001, 2009.
Chui, et al., "A chemically functionalizable nanoporous material," *Science*, 283:1148-50, 1999.
Couck, et al., "An amine-functionalized MIL-53 metal-organic framework with large separation power for CO2 and CH4," *J. Am. Chem. Soc.*, 131:6326-7, 2009.
Czepirski and Jagiello, "Virial-Type Thermal Equation of Gas-Solid Adsorption," *Chem. Eng. Sci.*, 44:797-801, 1989.
Dietzel, et al., "Adsorption properties and structure of $CO_2$ adsorbed on open coordination sites of metal-organic framework $Ni_2$(dhtp) from gas adsorption, IR spectroscopy and X-ray diffraction," *Chem. Common.*, pp. 5125-5127, 2008.
Dietzel, et al., "An in situ high-temperature single-crystal investigation of a dehydrated metal-organic framework compound and field-induced magnetization of one-dimensional metal-oxygen chains," *Angew. Chem. Int. Ed.*, 44:6354-8, 2005.
Dietzel, et al., "Hydrogen adsorption in a nickel based coordination polymer with open metal sites in the cylindrical cavities of the desolvated framework," *Chem. Commun.*, 959-61, 2006.
Dietzel, et al., "Structural changes and coordinatively unsaturated metal atoms on dehydration of honeycomb analogous microporous metal-organic frameworks," *Chemistry*, 14:2389-97, 2008.
Dincă and Long, "Hydrogen storage in microporous metal-organic frameworks with exposed metal sites," *Angew. Chem. Int. Ed. Engl.*, 47:6766-79, 2008.
Dybtsev, et al., "A homochiral metal-organic material with permanent porosity, enantioselective sorption properties, and catalytic activity," *Angew. Chem. Int. Ed.*, 45:916-920, 2006.
Eddaoudi, et al., "Modular chemistry: secondary building units as a basis for the design of highly porous and robust metal-organic carboxylate frameworks," *Acc. Chem. Res.*, 34:319-30, 2001.
Eddaoudi, et al., "Porous metal-organic polyhedra: 25 A cuboctahedron constructed from 12 Cu2(CO2)4 paddle-wheel building blocks," *J. Am. Chem. Soc.*, 123:4368-9, 2001.
Eddaoudi, et al., "Systematic design of pore size and functionality in isoreticular MOFs and their application in methane storage," *Science*, 295:469-72, 2002.
Fang, et al., "A metal-organic framework with the zeolite MTN topology containing large cages of vol. 2.5 $nm^3$" *Angew. Chem. Int. Ed.*, 44:3845-8, 2005.
Fang, et al., "A multifunctional metal-organic open framework with a bcu topology constructed from undecanuclear clusters," *Angew. Chem.*, 118:6272-6, 2006.
Fang, et al., "Mesoporous metal-organic framework with rare etb topology for hydrogen strorage and dye assembly," *Angew. Chem.*, 119:6758-62, 2007.

(56) References Cited

OTHER PUBLICATIONS

Férey, "Hybrid porous solids: past, present, future," *Chem. Soc. Rev.*, 37:191-214, 2008.
Férey, et al., "Hydrogen adsorption in the nanoporous metal-benzenedicarboxylate M(OH)O2C—C6H4—CO2) (M=Al3+, Cr3+), MIL-53," *Chem. Commun.*, pp. 2976-2977, 2003.
Furukawa, et al., "Independent verification of the saturation hydrogen uptake in MOF-177 and establishment of a benchmark for hydrogen adsorption in metal-organic frameworks," *J. Mater. Chem.*, 17:3197-204, 2007.
Hermes, et al., "Selective nucleation and growth of metal-organic open framework thin films on patterned COOH/CF3-terminated self-assembled monolayers on Au(111)," *J. Am. Chem. Soc.*, 127:13744-5, 2005.
Hou, et al., "Porous metal-organic framework based on mu4-oxo tetrazinc clusters: sorption and guest-dependent luminescent properties," *Inorg. Chem.*, 47:1346-51, 2008.
Hu, et al., "A new MOF-505 analog exhibiting high acetylene storage," *Chem. Commun.*, pp. 7551-3, 2009.
Huang, et al., "Shape-selective sorption and fluorescent sensing of aromatics in a flexible network of tetrakis[(4-methylthiophenyl)ethynyl]silane and AgBF$_4$," *Chem. Mater.*, 21:541-6, 2009.
Hwang, et al., "Amine grafting on coordinatively unsaturated metal centers of MOFs: consequences for catalysis and metal encapsulation," *Angew. Chem. Int. Ed.*, 47:4144-8, 2008.
International Search Report and Written Opinion, issued in PCT/US2010/023773, dated Apr. 1, 2010.
Jagiello, et al., "Adsorption near ambient temperatures of methane, carbon tetrafluoride, and sulfur hexafluoride on commercial activated carbons," *J. Chem. Eng. Data.*, 40:1288, 1995.
Kesanli, et al., "Highly interpenetrated metal-organic frameworks for hydrogen storage," *Angew. Chem. Int. Ed. Engl.*, 44:72-5, 2004.
Kitagawa, et al., "Functional porous coordination polymers," *Angew. Chem. Int. Ed.*, 43:2334-75, 2004.
Koder, et al., "Design and engineering of an $O_2$ transport protein," *Nature*, 458:305-9, 2009.
Koh, et al., "A porous coordination copolymer with over 5000 m2/g BET surface area," *J. Am. Chem. Soc.*, 131:4184-5, 2009.
Lan, et al., "A luminescent microporous metal-organic framework for the fast and reversible detection of high explosives," *Angew. Chem. Int. Ed.*, 48:2334-8, 2009.
Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [{Cu2(abtc)}3]," *Agnew. Chem. Int. Ed.*, 47:7741-5, 2008.
Lee, et al., "Synthesis and gas sorption properties of a metal-azolium framework material," *Inorg. Chem.*, 48:9971-3, 2009.
Li, et al., "Design and synthesis of an exceptionally stable and highly porous metal-organic framework," *Nature*, 402:276-9, 1999.
Lim, et al., "Cucurbit[6]uril: organic molecular porous material with permanent porosity, exceptional stability, and acetylene sorption properties," *Agnew. Chem.*, 120:3400-03, 2008.
Lin, et al., "High capacity hydrogen adsorption in Cu(II) tetracarboxylate framework materials: the role of pore size, ligand functionatization, and exposed metal sites," *J. Am. Chem. Soc.*, 131:2159-71, 2009.
Lin, et al., "Hydrogen, methane and carbon dioxide adsorption in metal-organic framework materials," *Top Curr. Chem.*, 293:35-76, 2010.
Lin, et al., "Modular synthesis of functional nanoscale coordination polymers," *Angew. Chem. Int. Ed.*, 48:650-8, 2009.
Liu, et al., "Increasing the density of adsorbed hydrogen with coordinatively unsaturated metal centers in metal-organic frameworks," *Langmuir*, 24:4772-7, 2008.
Liu, et al., "Metal-organic framework as a template for porous carbon synthesis," *J. Am. Chem. Soc.*, 130:5390-1, 2008.
Ma and Lin, "Unusual interlocking and interpenetration lead to highly porous and robust metal-organic frameworks," *Angew. Chem. Int. Ed.*, 48:3637-40, 2009.
Ma, et al., "Framework-Catenation Isomerism in MOFs and Its Impact on Hydrogen Uptake," *J. Am. Chem. Soc.*, 129:1858-9, 2007.
Ma, et al., "Further investigation of the effect of framework catenation on hydrogen uptake in metal-organic frameworks," *J. Am. Chem. Soc.*, 130:15896-902, 2008.
Ma, et al., "Metal-organic framework from an anthracene derivative containing nanoscopic cages exhibiting high methane uptake," *J. Am. Chem. Soc.*, 130:1012-6, 2008.
Matsuda, et al., "Highly controlled acetylene accommodation in a metal-organic microporous material," *Nature*, 436:238-41, 2005.
McKinlay, et al., "Exceptional behavior over the whole adsorption-storage-delivery cycle for NO in porous metal organic frameworks," *J. Am. Chem. Soc.*, 130:10440-10444, 2008.
Millward and Yaghi, "Metal-organic frameworks with exceptionally high capacity for storage of carbon dioxide at room temperature," *J. Am. Chem. Soc.*, 127:17998-9, 2005.
Morris and Wheatley, "Gas storage in nanoporous materials," *Angew. Chem. Int. Ed.*, 47:4966-81, 2008.
Mu, et al., "A novel metal-organic coordination polymer for selective adsorption of $CO_2$ over $CH_4$," *Chem. Commun.*, pp. 2493-5, 2009.
Mulfort and Hupp, "Chemical reduction of metal-organic framework materials as a method to enhance gas uptake and binding," *J. Am. Chem. Soc.*, 129:9604-5, 2007.
Myers and Prausnitz, "Thermodynamics of mixed-gas adsorption," *AIChE J.*, 11:121-7, 1965.
Nelson, et al., "Supercritical processing as a route to high internal surface areas and permanent microporosity in metal-organic framework materials" *J. Am. Chem. Soc.*, 131:458-60, 2009.
Noro, et al., "A new, methane adsorbent, porous coordination polymer," *Angew. Chem. Int. Ed. Engl.*, 39:2081-4, 2000.
Park, et al., "Exceptional chemical and thermal stability of zeolitic imidazolate frameworks," *Proc. Natl. Acad. Sci. USA*, 103:10186-91, 2006.
Reid and Thomas, "Adsorption kinetics and size exclusion properties of probe molecules for the selective porosity in a carbon molecular sieve used for air separation," *J. Phys. Chem. B.*, 105:10619-29, 2001.
Reid and Thomas, "Adsorption of gases on a carbon molecular sieve used for air separation: linear adsorptives as probes for kinetic selectivity," *Langmuir*, 15:3206-18, 1999.
Rieter, et al., "Nanoscale coordination polymers for platinum-based anticancer drug delivery," *J. Am. Chem. Soc.*, 130:11584-5, 2008.
Rosi, et al., "Hydrogen storage in microporous metal-organic frameworks," *Science*, 300:1127-9, 2003.
Rosi, et al., "Rod packings and metal-organic frameworks constructed from rod-shaped secondary building units," *J. Am. Chem. Soc.*, 127:1504-18, 2005.
Roswell and Yaghi, "Effects of functionalization, catenation, and variation of the metal oxide and organic linking units on the low-pressure hydrogen adsorption properties of metal-organic frameworks," *J. Am. Chem. Soc.*, 128:1304-15, 2006.
Samsonenko, et al., "Microporous magnesium and manganese formates for acetylene storage and separation," *Chem. Asian J.*, 2:484-8, 2007.
Seo, et al., "A homochiral metal-organic porous material for enantioselective separation and catalysis," *Nature*, 404:982-6, 2000.
Serre, et al., "Role of solvent-host interactions that lead to very large swelling of hybrid frameworks," *Science*, 315:1828-31, 2007.
Shimomura, et al., "Porous coordination polymers towards gas technology," *Struct. Bond*, 132:51-86, 2009.
Spek, "Single-crystal structure validation with the program PLATON," *J. Appl. Cryst.*, 36:7-13, 2003.
Stang and Diederich, In: *Modern Acetylene Chemistry*, VCH, New York, 1995.
Tanaka, et al., "Anthracene array-type porous coordination polymer with host-guest charge transfer interactions in excited states," *Chem. Commun.*, pp. 3142-3144, 2007.
Tanaka, et al., "Storage and sorption properties of acetylene in jungle-gym-like open frameworks," *Chem. Asian J.*, 3:1343-9, 2008.
Thallapally, et al., "Flexible (breathing) interpenetrated metal-organic frameworks for $CO_2$ separation applications," *J. Am. Chem. Soc.*, 130:16842-3, 2008.

(56) References Cited

OTHER PUBLICATIONS

Thomas, "Adsorption and desorption of hydrogen on metal-organic framework materials for storage applications: comparison with other nanoporous materials," *Dalton Trans.*, 1487-1505, 2009.
Thomas, "How far is the concept of isolated active sites valid in solid catalysts?" *Top Catal.*, 50:98-105, 2008.
Vitillo, et al., "Role of exposed metal sites in hydrogen storage in MOFs," *J. Am. Chem. Soc.*, 130:8386-96, 2008.
Wang, et al., "Bottom-up synthesis of porous coordination frameworks: apical substitution of a pentanuclear tetrahedral precursor," *Angew. Chem. Int. Ed.*, 48:5291-5, 2009.
Wang, et al., "Enhancing $H_2$ uptake by "close-packing" alignment of open copper sites in metal-organic framework," *Angew. Chem. Int. Ed.*, 47:7263-6, 2008.
Welbes and Borovik, "Confinement of metal complexes within porous hosts: development of functional materials for gas binding and catalysis," *Acc. Chem. Res.*, 38:765-74, 2005.
Wu, et al., "High-capacity methane storage in metal-organic frameworks M2(dhtp): the important role of open metal sites," *J. Am. Chem. Soc.*, 131:4995-5000, 2009.
Xiang, et al., "Exceptionally high acetylene uptake in a microporous metal-organic framework with open metal sites," *J. Am. Chem. Soc.*, 131:12415-9, 2009.
Xiang, et al., "Open metal sites within isostructural metal-organic frameworks for differential recognition of acetylene and extraordinarily high acetylene storage capacity at room temperature," *Angew. Chem. Int. Ed. Engl.*, 49:4615-8, 2010.
Xiao, et al., "High-capacity hydrogen and nitric oxide adsorption and storage in a metal-organic framework," *J. Am. Chem. Soc.*, 129:1203-9, 2007.
Xu, et al., "Robust metal-organic framework enforced by triple-framework interpenetration exhibiting high H2 storage density," *Inorg. Chem.*, 47:6825-8, 2008.
Xue, et al., "New prototype isoreticular metal-organic framework $Zn_4O(FMA)_3$ for gas storage," *Inorg. Chem.*,48:4649-51, 2009.
Xue, et al., "Structure, hydrogen storage, and luminescence properties of three 3D metal-organic frameworks and NbO and PtS topologies." *Crystal Growth & Design*, 8:2478-83, 2008.
Yang and Zhong, "Molecular simulation of carbon dioxide/methane/hydrogen mixture adsorption in metal-organic frameworks," *J. Phys. Chem. B.*, 110: 17776-83, 2006.
Yildirim and Hartman, "Direct observation of hydrogen adsorption sites and nanocage formation in metal-organic frameworks," *Phys. Rev. Lett.*, 95:215504, 2005.
Zhang and Chen, "Exceptional framework flexibility and sorption behavior of a multifunctional porous cuprous triazolate framework," *J. Am. Chem. Soc.*, 130:6010-7, 2008.
Zhang and Chen, "Optimized acetylene/carbon dioxide sorption in a dynamic porous crystal," *J. Am. Chem. Soc.*, 131:5516-21, 2009.
Zhang and Kitagawa, "Supramolecular isomerism, framework flexibility, unsaturated metal center, and porous property of Ag(I)/Cu(I) 3,3',5,5'-tetrametyl-4,4'-bipyrazolate," *J. Am. Chem. Soc.*, 130:907-17, 2008.
Zhang, et al., "A highly connected porous coordination polymer with unusual chnnel structure and sorption properties," *Angew. Chem. Int. Ed.*, 48:5287-90, 2009.
Zhang, et al., "Versatile structure-direction roles of deep-eutectic solvents and their implication in the generation of porosity and open metal sites for gas storage," *Angew. Chem. Int. Ed.*, 48:3486-90, 2009.
Zhang, et al., "Zeolitic boron imidazolate frameworks," *Angew. Chem. Int. Ed. Engl.*, 48:2542-5, 2009.
Zhao, et al., "Hysteretic adsorption and desorption of hydrogen by nanoporous metal-organic frameworks," *Science*, 306:1012-5, 2004.
Zhou and Yildirim, "Nature and tunability of enhanced hydrogen binding in metal-organic frameworks with exposed transition metal sites," *J. Phys. Chem. C*, 112:8132, 2008.
Zhou, et al., "Enhanced H2 adsorption in isostructural metal-organic frameworks with open metal sites: strong dependence of the binding strength on metal ions," *J. Am. Chem. Soc.*, 130:15268-9, 2008.

Bae, et al., "Separation of gas mixtures using Co(II) carborane-based porous coordination polymers," *Chem. Commun.*, 46:3478-80, 2010.
Chen, et al., "Porous Cu—Cd mixed-metal-organic frameworks constructed from Cu(Pyac)2 [Bis[3-(4-pyridyl)pentane-2,4-dionato]copper(II)]," *Inorg. Chem.*, 43:8209-11, 2004.
Cho, et al., "A metal-organic framework material that functions as an enantioselective catalyst for olefin epoxidation," *Chem. Commun.* pp. 2563-2565, 2006.
Deng, et al., "Multiple functional groups of varying ratios in metal-organic frameworks," *Science*, 327:846-50, 2010.
Devic, et al., "Functionalization in flexible porous solids: effects on the pore opening and the host-guest interactions," *J. Am. Chem Soc.*, 132:1127-36, 2010.
Dubbeldam, et al., "Separation and molecular-level segregation of complex alkane mixtures in metal-organic frameworks," *J. Am. Chem. Soc.*, 130:10884-5, 2008.
Dybtsev, et al., "Microporous manganese formate: a simple metal-organic porous material with high framework stability and highly selective gas sorption properties," *J. Am. Chem. Soc.*, 126:32-3, 2004.
Eddaoudi, et al., "Highly porous and stable metal-organic framework: structure design and sorption properties," *J. Am. Chem. Soc.*, 122:1391-7, 2000.
Fang, et al., "Microporous metal-organic framework constructed from heptanuclear zinc carboxylate secondary building units," *Chem. Eur. J.*, 12:3754-8, 2006.
Finsy, et al., "Pore-filling-dependent selectivity effects in the vapor-phase separation of xylene isomers on the metal-organic framework MIL-47," *J. Am. Chem. Soc.*, 130:7110-8, 2008.
Horike, et al., "Soft porous crystals," *Nat. Chem.*, 1:695-704, 2009.
Kitaura, et al., "Immobilization of a metallo schiff base into a microporous coordination polymer," *Angew. Chem. Int. Ed. Engl.*, 43:2684-7, 2004.
Kunznicki, et al., "A titanosilicate molecular sieve with adjustable pores for size-selective adsorption of molecules," *Nature*, 412:720-4, 2001.
Li, et al., "Zeolitic imidazolate frameworks for kinetic separation of propane and propene" *J. Am. Chem. Soc.*, 131:10368-9, 2009.
Liu, et al., "Engineering homochiral metal-organic frameworks for heterogeneous asymmetric catalysis and enantioselective separation," *Adv. Mater.*, 22:4112-35, 2010.
Ma, et al., "Preparation and gas adsorption studies of three mesh-adjustable molecular sieves with a common structure," *J. Am. Chem. Soc.*, 131:6445-51, 2009.
Ma, et al., "A series of isoreticular chiral metal-organic frameworks as a tunable platform for asymmetric catalysis," *Nat. Chem.*, 2:838-46, 2010.
Morris and Bu, "Induction of chiral porous solids containing only achiral building blocks," *Nat. Chem.*, 2:353-61, 2010.
Murray, et al., "Highly-selective and reversible $O_2$ binding in $Cr_3$(1,3,5-benzenetricarboxylate)$_2$," *J. Am. Chem. Soc.*, 132:7856-7, 2010.
Nuzhdin, et al., "Enantioselective chromatographic resolution and one-pot synthesis of enantiomerically pure sulfoxides over a homochiral Zn-organic framework," *J. Am. Chem. Soc.*, 129:12958-9, 2007.
O'Keeffe, et al., "The Reticular Chemistry Structure Resource (RCSR) database of, and symbols for, crystal nets," *Acc. Chem. Res.*, 41:1782-9, 2008.
Rabone, et al., "An adaptable peptide-based porous material," *Science*, 329:1053-7, 2010.
Shimomura, et al., "Selective sorption of oxygen and nitric oxide by an electron-donating flexible porous coordination polymer," *Nat. Chem.*, 2:633-7, 2010.
Vaidhyanathan, et al., "A family of nanoporous materials based on an amino acid backbone," *Angew. Chem. Int. Ed. Engl.*, 45:6495-9, 2006.
Xie, et al., "Porous phosphorescent coordination polymers for oxygen sensing," *J. Am. Chem. Soc.*, 132:922-3, 2010.
Yang, et al., "Cation-induced kinetic trapping and enhanced hydrogen adsorption in a modulated anionic metal-organic framework," *Nat. Chem.*, 1:487-93, 2009.

\* cited by examiner

$Zn_5(BTA)_6(TDA)_2$—A ROBUST HIGHLY INTERPENETRATED METAL-ORGANIC FRAMEWORK CONSTRUCTED FROM PENTANUCLEAR CLUSTERS FOR SELECTIVE SORPTION OF GAS MOLECULES

This application claims the benefit of priority to U.S. Provisional Application No. 61/575,375, filed Aug. 19, 2011, the entire disclosure of which is specifically incorporated herein by reference.

This invention was made with government support under grant number CHE 0718281 from the National Science Foundation. The government has certain rights in the invention

BACKGROUND OF THE INVENTION

I. Field of the Invention

The present disclosure relates generally to the fields of chemistry and materials science. More particularly, it concerns metal-organic frameworks, compositions thereof and methods use thereof, including for storing, detecting, and separating of gas and/or liquid molecules.

II. Description of Related Art

Microporous metal-organic frameworks (MOFs) have been rapidly emerging as new type of porous materials for gas storage, separation, sensing and heterogeneous catalysis. The tunable pores and the immobilized functional sites within such microporous MOFs have enabled them to direct specific recognition of certain molecules, and thus for their highly selective guest sorption and separation. The diverse metal ions and/or metal-containing clusters as the nodes and a variety of organic linkers as the bridges to construct the porous coordination polymers (PCPs) by the coordination bonds have led to a series of porous MOFs from ultramicroporous to mesoporous domains. Although thousands of MOFs have been synthesized and structurally characterized over the past two decades, those exhibiting permanent porosity and thus being classified as porous MOFs are still of few percentage. This is primarily due to the labile coordination geometries of the metal ions and/or metal-containing clusters, and the flexibility of the bridging organic linkers which cannot sustain the frameworks under vacuum and/or thermal activation. One efficient strategy to stabilize the PCPs and thus to construct porous MOFs is to make use of rigid clusters (Fang et al., 2006a; Fang et al., 2006b; Bai et al., 2008; Wang et al., 2009), as exemplified in those MOFs with the binuclear paddlewheel $M_2(COO)_6$ ($M=Cu^{2+}$, $Co^{2+}$, $Ni^{2+}$ and $Zn^{2+}$) and tetranuclear $Zn_4O(COO)_6$ as the secondary building units (Eddaoudi et al., 2000). Another strategy to stabilize the frameworks is to make use of the framework interpenetration and/or interwoven to enforce the framework interactions (Ma and Lin, 2009; Kesanli et al., 2005). This approach has been successful in constructing interpenetrated MOFs with higher permanent porosity than their non-interpenetrated analogues (Ma et al., 2007; Ma et al., 2008).

Although thousands of MOFs have been synthesized and structurally characterized over the past two decades, the ones with open metal sites are still relatively few (Chen et al., 2010; Dinca and Long, 2008), this is mainly because such open metal sites are typically very reactive and tend to bind the atoms from the neighboring ligands to form the condensed structures. Also, few MOFs have been shown to be useful for selective sorption, separation and/or sensing of guest molecules. Accordingly, identifying and developing materials and compositions that exhibit one or more of these useful properties is desirable.

SUMMARY OF THE INVENTION

Disclosed herein is a new metal organic framework based on the formula comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid. In some embodiments, the method further comprises one or more than one type of guest molecule. In some embodiments, the guest molecule is a solvent molecule. In some embodiments, the solvent molecule is water, N,N'-diethylformamide or N,N'-dimethylformamide. In some embodiments, the guest molecule is a gas molecule. In some embodiments, the gas molecule is $H_2$, $N_2$, Ar, $O_2$, $CO_2$, NO, $NO_2$ or CO.

In some embodiments, the guest molecule is an alkane$_{(C1-6)}$, alkene$_{(C2-4)}$, alkyne$_{(C2-6)}$, alcohol$_{(C1-6)}$, arene$_{(C6-8)}$ or a substituted version of any of these. In some embodiments, the alkane$_{(C1-6)}$ is $CH_4$, $C_2H_6$, $C_3H_8$, $C_4H_{10}$, $C_5H_{12}$ or $C_6H_{14}$. In some embodiments, the alkane$_{(C1-6)}$ is a cycloalkane$_{(C3-6)}$ selected from the group consisting of $C_3H_6$, $C_4H_8$, $C_5H_{10}$ and $C_6H_{12}$. In some embodiments, the alkene$_{(C2-6)}$ is $C_2H_4$, $C_3H_6$, $C_4H_8$, $C_5H_{10}$ or $C_6H_{12}$. In some embodiments, the alkyne$_{(C2-6)}$ is $C_2H_2$. In some embodiments, the alcohol$_{(C1-6)}$ is methanol, ethanol, n-propanol, isopropanol, n-butanol or isobutanol. In some embodiments, the guest molecule is an arene$_{(C6-8)}$ or a substituted arene$_{(C6-8)}$. In some embodiments, the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene.

In some embodiments, the MOF is substantially free from any solvent molecules. In some embodiments, the MOF has a weight percentage at least 90% attributable to repeat units of the formula $Zn_5(BTA)_6(TDA)_2$. In some embodiments, the MOF has a weight percentage at least 95% attributable to repeat units of the formula $Zn_5(BTA)_6(TDA)_2$. In some embodiments, the MOF has a weight percentage at least 99% attributable to repeat units of the formula $Zn_5(BTA)_6(TDA)_2$.

In another aspect the present disclosure provides a method of storing a compound within a metal-organic framework (MOF) comprising:
 (a) obtaining MOF comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid; and
 (b) combining the MOF with a first compound such that the first compound is stored within the MOF.

In another aspect the present disclosure provides a method of detecting a compound using an MOF comprising:
 (a) obtaining a MOF comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid;
 (b) combining the MOF with a first compound such that the first compound enters the MOF to form an MOF•guest complex; and
 (c) comparing the luminescence intensity of the MOF with the luminescence intensity of the MOF•guest complex so as to detect the first compound.

In another aspect the present disclosure provides a method of separating two or more compounds using an MOF comprising:

(a) obtaining a metal-organic framework (MOF) comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid;

(b) combining the MOF with a mixture comprising a first compound and a second compounds; and (c) separating the two or more compounds based on their differential diffusion rate within the MOF.

In some embodiments, the first compound is in the form of a gas or a liquid. In some embodiments, the first compound is an alkane$_{(C1-6)}$, alkene$_{(C2-4)}$, alkyne$_{(C2-6)}$, alcohol$_{(C1-6)}$, arene$_{(C6-8)}$ or a substituted version of any of these. In some embodiments, the alkane$_{(C1-6)}$ is $CH_4$, $C_2H_6$, $C_3H_8$, $C_4H_{10}$, $C_5H_{12}$ or $C_6H_{14}$. In some embodiments, the alkane$_{(C1-6)}$ is $CH_4$. In some embodiments, the second compound is ethylene. In some embodiments, the alkane$_{(C1-6)}$ is a cycloalkane$_{(C3-6)}$ selected from the group consisting of $C_3H_6$, $C_4H_8$, $C_5H_{10}$ and $C_6H_{12}$. In some embodiments, the alkene$_{(C2-6)}$ is $C_2H_4$, $C_3H_6$, $C_4H_8$, $C_5H_{10}$ or $C_6H_{12}$. In some embodiments, the alkene$_{(C2-6)}$ is $C_2H_4$. In some embodiments, the second compound is $CO_2$. In some embodiments, the alkyne$_{(C2-6)}$ is $C_2H_2$. In some embodiments, the alcohol$_{(C1-6)}$ is methanol, ethanol, n-propanol, isopropanol, n-butanol or isobutanol. In some embodiments, the first compound is an arene$_{(C6-8)}$ or a substituted arene$_{(C6-8)}$. In some embodiments, the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene. In some embodiments, the substituted arene$_{(C6-8)}$ is nitrobenzene. In some embodiments, the first compound is carbon dioxide. In some embodiments, the first compound is carbon monoxide. In some embodiments, the first compound is oxygen or nitrogen. In some embodiments, the first compound is $F_2$ or $Cl_2$. In some embodiments, the first compound is a noble gas. In some embodiments, the first compound is an alcohol. In some embodiments, the alcohol is methanol, ethanol, n-propanol or isopropanol.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

FIGS. 1a&b.

FIGS. 2a-e: FIG. 2b shows the dia net viewed down the b axis. FIG. 2c shows the large adamantanoid cages (yellow). FIG. 2d shows the fourfold interpenetration diamond networks give two kinds of channels along both a and b axes: a long and narrow one (pink) sites between the yellow and red networks, another quasi-square one (cyan) does between the blue and green networks. FIG. 2e shows the fourfold interpenetrated framework exhibiting the channels along the a axis.

DESCRIPTION OF ILLUSTRATIVE EMBODIMENTS

Disclosed herein are robust highly interpenetrated metal-organic frameworks constructed from pentanuclear clusters. These may be used for applications such as selective gas storage, selective gas sorption and selective gas separation.

I. Definitions

MOF 1 corresponds to the formula $Zn_5(BTA)_6(TDA)_2.15DMF.8H_2O$. MOF 1a corresponds to the formula $Zn_5(BTA)_6(TDA)_2$.

BTA refers to the deprotonated anion of 1H-benzo[d][1,2,3]triazole.

TDA refers to the deprotonated dianion of thiophene-2,5-dicarboxylic acid.

DMF refers to N,N'-dimethylformamide.

"Guest molecules" refer to molecules, including solvent molecules and gas molecules, that are enclosed within the pores or open sites of a framework material such as a MOF. Examples of guest molecules include, for example, methane, water, N,N'-dimethylformamide, N,N'-diethylformamide, ethanol and nitrobenzene.

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit (see below), that is without brackets or the subscript n.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Interpenetrating metal-organic framework" is defined as metal-organic frameworks interlocked with one another.

"Multidentate organic linker" is defined as ligand having several binding sites for the coordination to one or more metal ions.

When used in the context of a chemical group, "hydrogen" means —H; "hydroxy" means —OH; "oxo" means =O; "halo" means independently —F, —Cl, —Br or —I; "amino" means —NH$_2$, and "nitro" means —NO$_2$.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkane" when used without the "substituted" modifier refers to a non-aromatic hydrocarbon consisting only of saturated carbon atoms and hydrogen and having a linear or branched, cyclo, cyclic or acyclic structure. Thus, as used herein cycloalkane is a subset of alkane. The compounds CH$_4$ (methane), CH$_3$CH$_3$ (ethane), CH$_3$CH$_2$CH$_3$ (propane), (CH$_2$)$_3$ (cyclopropane), CH$_3$CH$_2$CH$_2$CH$_3$ (n-butane), and CH$_3$CH(CH$_3$)CH$_3$ (isobutane), are non-limiting examples of alkanes. A "substituted alkane" differs from an alkane in that it also comprises at least one atom independently selected from the group consisting of N, O, F, Cl, Br, I, Si, P, and S. The following compounds are non-limiting examples of substituted alkanes: CH$_3$OH, CH$_3$Cl, nitromethane, CF$_4$, CH$_3$OCH$_3$ and CH$_3$CH$_2$NH$_2$.

The term "alkene" when used without the "substituted" modifier refers to a non-aromatic hydrocarbon having at least one carbon-carbon double bond and a linear or branched, cyclo, cyclic or acyclic structure. Thus, as used herein, cycloalkene is a subset of alkene. The compounds C$_2$H$_4$ (ethylene), CH$_3$CH=CH$_2$ (propene) and cylcohexene are non-limiting examples of alkenes. A "substituted alkene" differs from an alkene in that it also comprises at least one atom independently selected from the group consisting of N, O, F, Cl, Br, I, Si, P, and S.

The term "alkyne" when used without the "substituted" modifier refers to a non-aromatic hydrocarbon having at least one carbon-carbon triple bond and a linear or branched, cyclo, cyclic or acyclic structure. Thus, as used herein, cycloalkene is a subset of alkene. The compounds C$_2$H$_2$ (acetylene), CH$_3$CCH (propene) and cylcooctyne are non-limiting examples of alkenes. A "substituted alkene" differs from an alkene in that it also comprises at least one atom independently selected from the group consisting of N, O, F, Cl, Br, I, Si, P, and S.

The term "alcohol" when used without the "substituted" modifier corresponds to an alkane, as defined above, wherein at least one of the hydrogen atoms has been replaced with a hydroxy group. Alcohols have a linear or branched, cyclo, cyclic or acyclic structure. The compounds methanol, ethanol and cyclohexanol are non-limiting examples of alcohols. A "substituted alkane" differs from an alcohol in that it also comprises at least one atom independently selected from the group consisting of N, F, Cl, Br, I, Si, P, and S.

The term "arene" when used without the "substituted" modifier refers to an hydrocarbon having at least one six-membered aromatic ring. One or more alkyl, alkenyl or alkynyl groups may be optionally attached to this ring. Also this ring may optionally be fused with other rings, including non-aromatic rings. Benzene, toluene, naphthalene, and biphenyl are non-limiting examples of arenes. A "substituted arene" differs from an arene in that it also comprises at least one atom independently selected from the group consisting of N, O, F, Cl, Br, I, Si, P, and S. Phenol and nitrobenzene are non-limiting examples of substituted arenes.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

The metal-organic framework [$Zn_5(BTA)_6(TDA)_2 \cdot 15DMF \cdot 8H_2O$]$\cdot xG$ (HBTA=1,2,3-benzenetriazole; $H_2TDA$=Thiophene-2,5-dicarboxylic acid G=one or more optional guest molecules) may be made using the methods outlined in the examples section below.

For example, MOF 1 can be readily constructed by the solvothermal reaction of $Zn(NO_3)_2 \cdot 6H_2O$, HBTA, and $H_2TDA$ in DMF/ethanol/$H_2O$ mixture at 100° C. for 24 hrs as colorless octahedron-shaped crystals. It was formulated as $Zn_5(BTA)_6(TDA)_2 \cdot 15DMF \cdot 8H_2O$ (DMF=N,N'-dimethylformamide) by elemental microanalysis and single-crystal X-ray diffraction studies, and the phase purity of the bulk material was independently confirmed by powder X-ray diffraction (PXRD) and thermogravimetric analysis (TGA) (details in Examples section below).

Figure 2A:
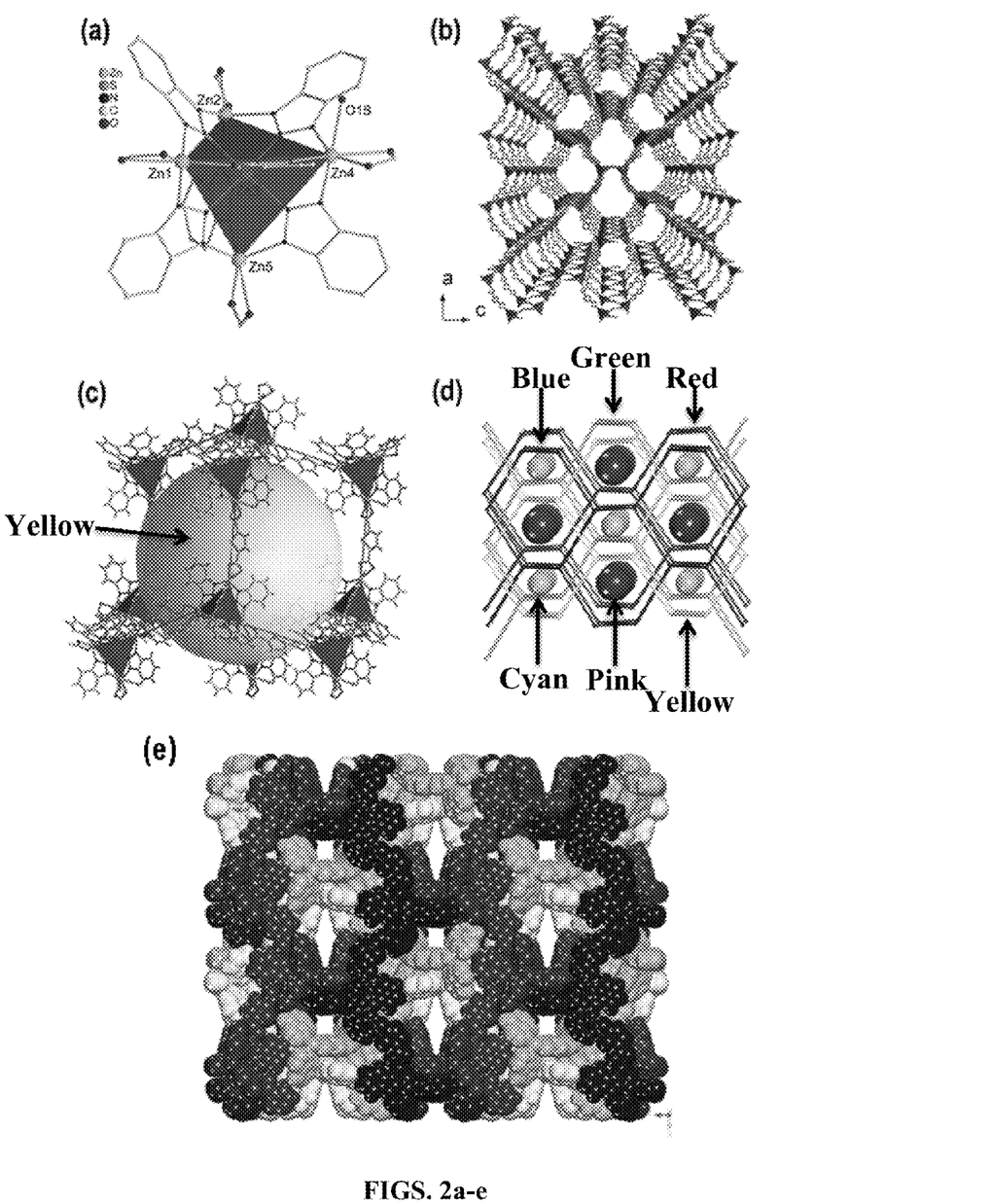
FIG. 2a shows a $\{Zn_5(BZA)_6(O_{solvent})\}$ cluster linked by four TDA molecules to form a single dia net.

A single-crystal X-ray crystallographic study revealed that MOF 1 crystallizes in tetragonal space group $I4_1/a$. MOF 1 is a three-dimensional open-framework structure comprising {$Zn_5(BTA)_6(O_{solvent})$} clusters as tetrahedral nodes, which were linked to four crystallographically independent clusters by the extended TDA ligands via their carboxylate groups to give a diamond network (FIG. 2b). Within the {$Zn_5(BTA)_6(O_{solvent})_4$} cluster, the Zn3 ion is located at the center is surrounded by six N atoms from six BTAs, while the coordination environments of the other four at each vertex of the tetrahedron were completed by three N atoms from three BTAs and two O atoms from TDA linkers (FIG. 2a). One of the four vertical Zn ions (Zn4) is further bounded to one O atom of the solvent molecule, indicating the potential to have the open metal sites for their recognition of the gas molecules once the MOF 1 was thermally activated. The adamantanoid cages in a single dia net have a dimension of ca. 26 Å in diameter (FIG. 2c). The spacious nature of the single network allows three other identical dia networks to penetrate it in a normal mode, thus resulting in a four-fold interpenetrating dia array (FIG. 2d). Despite the interpenetration, the framework of MOF 1 remains open, and contains one-dimensional channels of ca. 4.1×10.0 Å$^2$ (pink) and 3.4×4.1 Å$^2$ (cyan) along the [1 0 0] and [0 1 0] directions that are occupied by disordered solvent molecules. PLATON (Spek, 2003) analysis showed that the effective free volume of MOF 1 is 37% of the crystal volume.

Figure 1A:
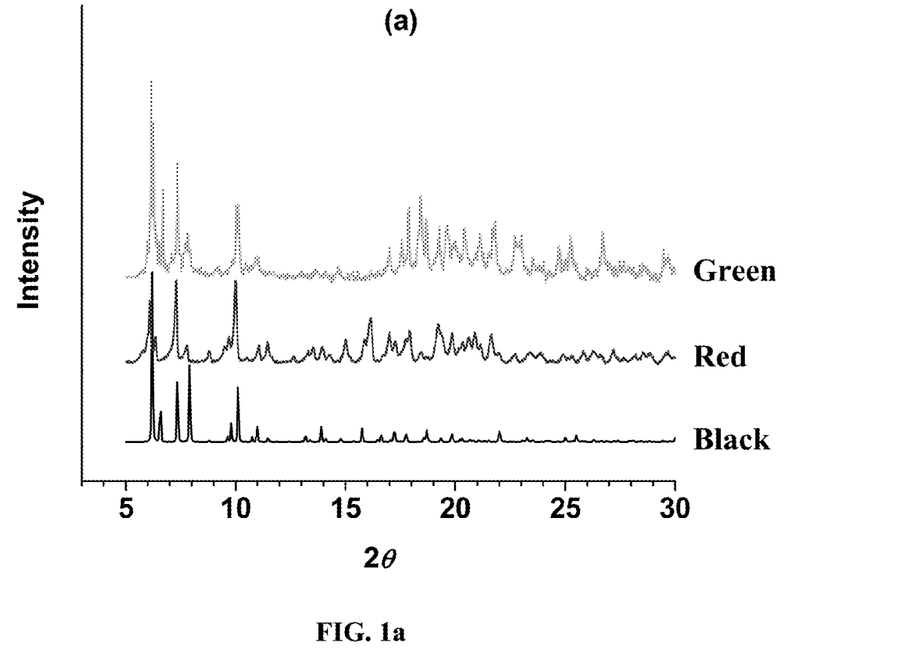
FIG. 1a shows PXRD patterns of the simulated pattern (black), the as-synthesized 1 (green), and the activated 1a (red).
Figure 1B:
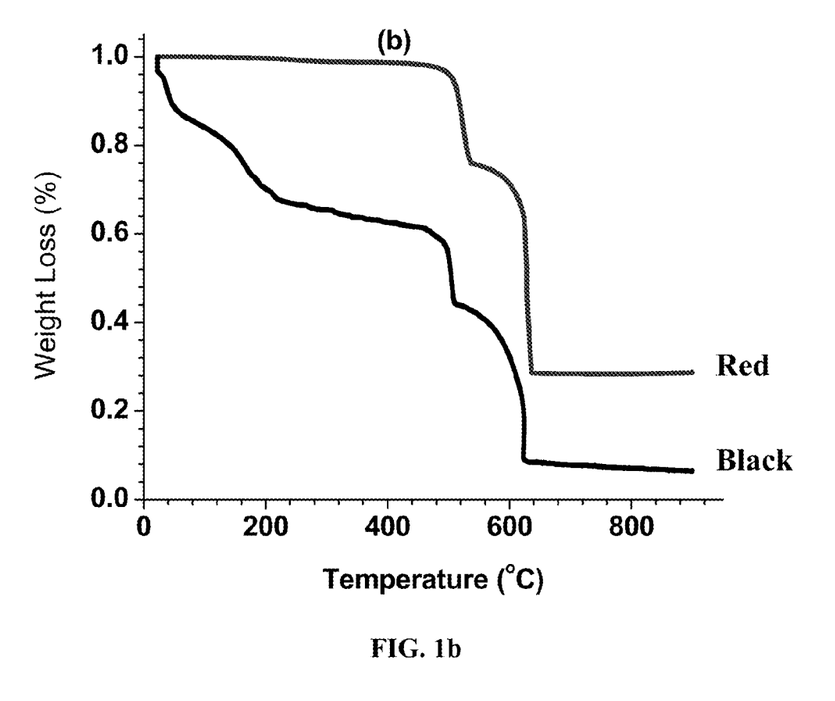
FIG. 1b shows TGA traces of the as-synthesized 1 (black) and the activated 1a (red) ranging from room temperature to 900° C.
Figure 3:
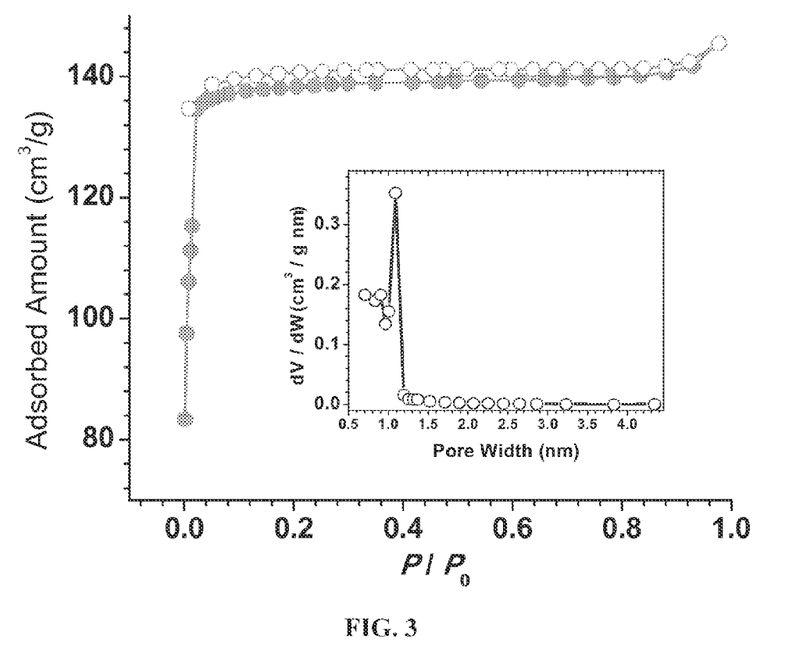
FIG. 3 shows the isothermal adsorption curve of $N_2$ gas for 1a. Inset: Horvath-Kawazoe pore size distribution plot.

Thermogravimetric analysis (TGA) of MOF 1 showed that approximately 40% weight loss occurred from 23° C. to 450° C., which is attributed primarily to the release of solvent molecules and coordinated solvent molecules (FIG. 1b). PXRD studies indicate that the activated 1 (MOF 1a) at 150° C. under high vacuum overnight keeps the high crystalline feature whose pattern matches with that of the as-synthesized 1, indicating that the framework of MOF 1 is robust (FIG. 1a). $N_2$ sorption isotherm at 77 K shows that the MOF 1a displays typical Type-I sorption behavior with the BET surface area of 414 m$^2$ g$^{-1}$ (Langmuir surface area, 607 m$^2$ g$^{-1}$) and pore volume of 0.24 cm$^3$ g$^{-1}$ (estimated by using Dubinin-Radushkevich equation), respectively (FIG. 3) (Roquerol et al., 1999). A fit of the adsorption data to the Horvath-Kawazoe model shows the maximum pore size in the range of 1.0-1.1 nm, in agreement with the structural analysis above.

The methods described above can be further modified, optimized and scaled up using the principles and techniques of chemistry and/or materials science as applied by a person skilled in the art. Such principles and techniques are taught, for example, in Chen et al. (2005), which is incorporated by reference herein.

III. Properties and Uses of MOFs

Figure 4:
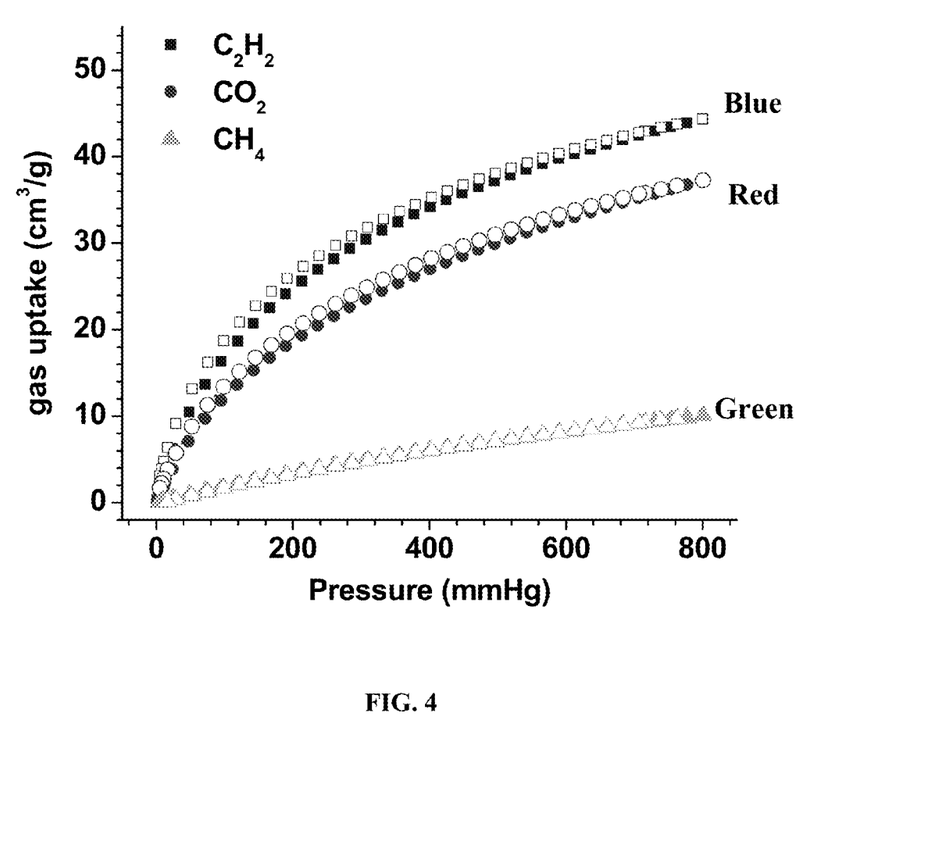
FIG. 4 shows the adsorption (solid) and desorption (open) isotherms of activated 1 at 295 K (acetylene (blue); carbon dioxide (red); and methane (green)).

In some embodiments the MOFs disclosed herein my be used for gas separation, gas detection and/or gas storage. Many of these applications result from the unique micropores of the MOFs. The establishment of permanent porosity of MOF 1a enables us to examine its potential application on the selective gas separation. As shown in FIG. 4, MOF 1a can take differential amount of $C_2H_2$ (44 cm$^3$/g), $CO_2$ (37 cm$^3$/g) and $CH_4$ (10 cm$^3$/g) at 1 atm and 295 K, highlighting MOF 1a as the promising material for the selective separation of $C_2H_2$/$CH_4$ and $CO_2$/$CH_4$ at room temperature. Such selective sorption of MOF 1a with respect to these three gas molecules are mainly attributed to their different interactions with the framework surfaces.

Figure 5:
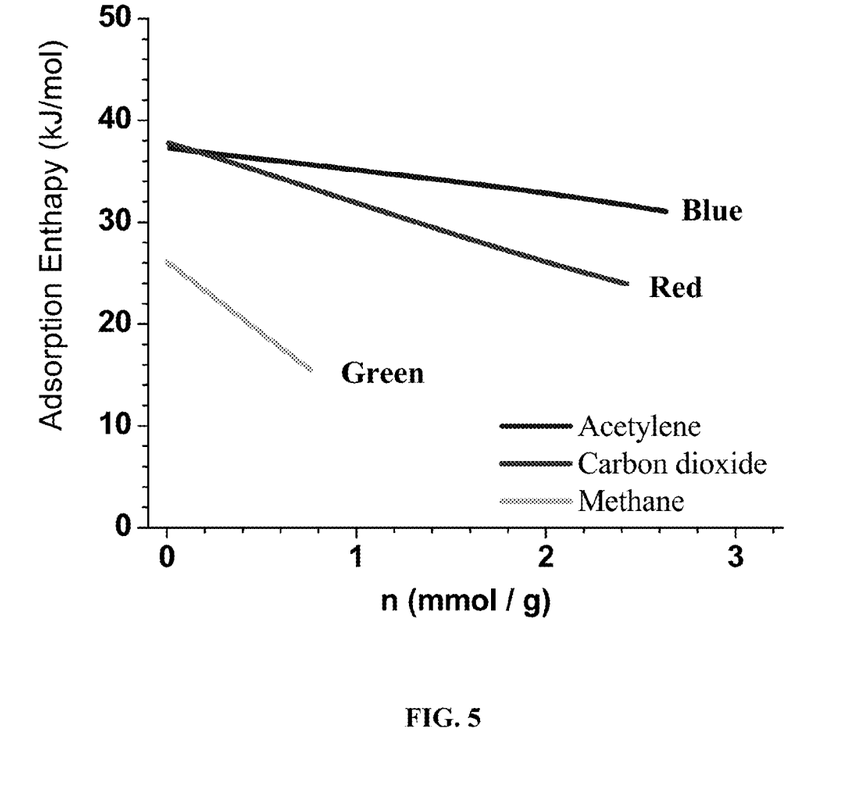
FIG. 5 shows the heat of adsorption of the activated 1 for acetylene (blue), carbon dioxide (red) and methane (green).

The coverage-dependent adsorption enthalpies of MOF 1a to these three gases, calculated based on virial method, a well established and reliable methodology from fits of their adsorption isotherms at 273 and 295 K (Roswell and Yaghi, 2006, which are both incorporated herein by reference). The enthalpies at zero coverage are 37.3, 37.8 and 26.1 kJ/mol for $C_2H_2$, $CO_2$ and $CH_4$, respectively (FIG. 5). These values of adsorption enthalpies are systematically high. In fact, the acetylene adsorption enthalpy of MOF 1a is much higher than that of 24.0 kJ/mol of Zn-MOF-74 with well orientated open $Zn^{2+}$ sites (Xiang et al., 2010). Such systematically larger enthalpies for gas adsorption might be attributed to both the possible open Zn4 sites and the optimized pore surface/curvature for their enhanced interactions with the gas molecules (Xie et al., 2010).

Figure 6:
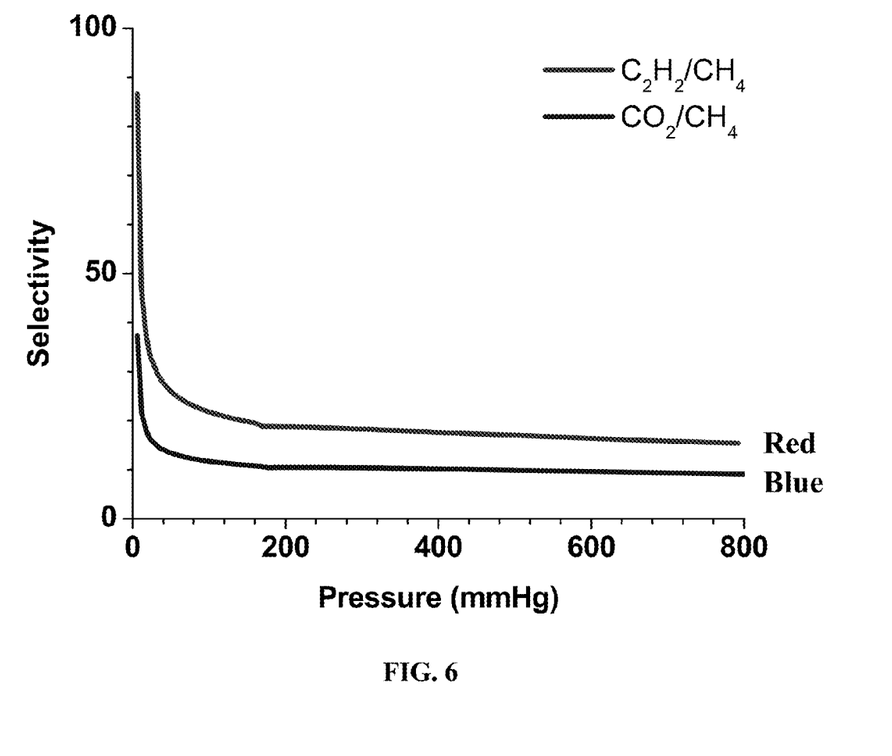
FIG. 6 shows the selectivity of $C_2H_2/CH_4$ (red) and $CO_2/CH_4$ (blue) in 1a for equimolar mixtures at 295 K.

The separation capabilities of MOF 1a for the selective $CO_2$/$CH_4$ and $C_2H_2$/$CH_4$ separation have been further examined by the ideal adsorbed solution theory (IAST). The calculated ideal adsorbed solution theory (IAST) selectivities (Myers, A. L.; Prausnitz' 1965; Mu et al., 2009; Lee et al., 2009; Babarao et al., 2007; Yang and Zhong, 2006) are shown in FIG. 6. The Langmuir-Freundlich model was applied to fit the experimental isotherms with excellent results (R>0.999), and IAST calculations were performed under equimolar mixture conditions. MOF 1a displays very high selectivities for $CO_2$ at low pressure. At about 6 mmHg, the $CO_2$/$CH_4$ and $C_2H_2$/$CH_4$ separation selectivity is 37 and 87, respectively. The selectivity decreases with increasing bulk pressure as zinc sites become inaccessible. The calculated selectivity for equimolar $CO_2$/$CH_4$ and $C_2H_2$/$CH_4$ is about 9.2 and 15.5, respectively, at 1 atm and 295 K, while the Henry's sectivities obtained from the virial method toward $CO_2$/$CH_4$ and $C_2H_2$/$CH_4$ are respectively of 12.0 and 22.3 at 295 K (Table 1). These values are moderately high compared with those well examined microporous MOFs (Myers, A. L.; Prausnitz' 1965; Mu et al., 2009; Lee et al., 2009; Babarao et al., 2007; Yang and Zhong, 2006). The possible open Zn4 sites within MOF 1a may enforce their stronger interactions with $C_2H_2$ and $CO_2$.

TABLE 1

Virial Coefficients Employed to Fit the 273.2 K and 295.0 K Adsorption Isotherm data of $C_2H_2$, $CO_2$ and $CH_4$ for MOF 1a.

|     | $C_2H_2$ | $CO_2$ | $CH_4$ |
| --- | --- | --- | --- |
| a0 | −4487.4 ± 15.2 | −4550.9 ± 79.1 | −3138.8 ± 198.4 |
| a1 | 282.8 ± 6.8 | 383.2 ± 71.7 | 1685.8 ± 595.7 |
| a2 | −32.4 ± 5.9 | 53.3 ± 17.3 | 0 ± 0 |
| a3 | 12.8 ± 1.4 | −20.9 ± 4.7 | 0 ± 0 |
| a4 | 0 ± 0 | 0 ± 0 | 0 ± 0 |
| a5 | 0 ± 0 | 0 ± 0 | 0 ± 0 |
| a6 | 0 ± 0 | 0 ± 0 | 0 ± 0 |
| b0 | 19.4 ± 0.1 | 20.2 ± 0.3 | 17.9 ± 0.7 |
| b1 | 0 ± 0 | −1.6 ± 0.3 | −5.5 ± 2.1 |
| b2 | 0 ± 0 | 0 ± 0 | 0.2 ± 0.1 |
| b3 | 0 ± 0 | 0 ± 0 | 0 ± 0 |
| R * | 1.000 | 1.000 | 0.943 |

* R is the correlation coefficient.

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Materials and Measurements.

All reagents and solvents employed were commercially available and used as supplied without further purification. Thermogravimetric (TGA) data were obtained on a TGA G500 V5.3 Build 171 instrument with a heating rate of 5° C./min under a $N_2$ atmosphere. Powder X-ray diffraction (PXRD) patterns were obtained with a Scintag X1 powder diffractometer system using Kα radiation with a variable divergent slit and a solid-state detector. The routine power was 1400 W (40 kV, 35 mA). Low-background quartz XRD slides (Gem Depot, Inc., Pittsburgh, Pa.) were used. For analyses, powder samples were dispersed on glass slides.

Synthesis of MOF 1:

A mixture of $Zn(NO_3)_2 \cdot 6H_2O$ (1.487 g, 5 mmol), HBTA (0.715 g, 6 mmol), and $H_2TDA$ (0.344 g, 2 mmol) were dissolved in the mixed DMF-ethanol-water (70/70/70 mL) solution and heated in a vial (400 mL) at 100° C. for 24 h. The colorless octahedron-shaped crystals formed were collected, washed with DMF and dried in air (1.883 g; Yield: 72%). Elem. anal. Calcd for $Zn_5(BTA)_6(TDA)_2 \cdot 15DMF \cdot 8H_2O$ ($C_{93}H_{149}N_{33}O_{31}S_2Zn_5$): C, 42.69; H, 5.74; N, 17.67. Found: C, 42.84; H, 5.81; N, 17.65. Sample of MOF 1 was soaked in methanol, filtered and activated under high vacuum at 150° C. overnight to get MOF 1a.

Single-Crystal X-Ray Crystallography:

Single crystal X-ray data of MOF 1 were collected using the microcrystal diffraction beamline 15ID-B at the Advanced Photon source in Argonne National Laboratory. Data were collected on Bruker D8 Diffractometer equipped with APEX II detector. Data integration and reduction were using APEX suite software. The structure was solved by direct methods and subsequent difference Fourier syntheses and refined using the SHELXTL software package. The H atoms on the ligand were placed in idealized positions and refined using a riding model. The H atoms on the coordinated solvent 0 atoms could not be located. The unit cell includes a large region of disordered solvent molecules, which could not be modeled as discrete atomic sites. PLATON/SQUEEZE was used to calculate the diffraction contribution of the solvent molecules and thereby producing a set of solvent-free diffraction intensities (Spek, 2003).

Gas Sorption Measurements:

A Micromeritics ASAP 2020 surface area analyzer was used to measure gas adsorption. In order to remove guest solvent molecules in the framework, the fresh sample soaked in methanol was filtered and vacuumed at 150° C. overnight. A sample of 150.0 mg was used for the sorption measurement and was maintained at 77 K with liquid nitrogen and 273 K with ice-water bath (slush), respectively. As the center-controlled air condition was set up at 22.0° C., a water bath of 22.0° C. was used for adsorption isotherms at 295.0 K.

Derivation of the Isosteric Heats of Adsorption:

A virial type expression of the following form was used to fit the combined isotherm data for a given material at 295.0 and 273.2 K (Roswell and Yaghi, 2006).

$$\ln P = \ln N + 1/T \sum_{i=0}^{m} a_i N^i + \sum_{i=0}^{n} b_i N^i. \quad (1)$$

Here, P is the pressure expressed in Torr, N is the amount adsorbed in mmol/g, T is the temperature in K, $a_i$ and $b_i$ are virial coefficients, and m, n represents the number of coefficients required to adequately describe the isotherms. The equation was fit using the statistical software package SPSS 16.0. m and n were gradually increased until the contribution of extra added a and b coefficients was deemed to be statistically insignificant towards the overall fit, as determined using the average value of the squared deviations from the experimental values was minimized. In all cases, m≤6 and n≤3. The values of the virial coefficients $a_0$ through $a_m$ were then used to calculate the isosteric heat of adsorption using the following expression.

$$Q_{st} = -R \sum_{i=0}^{m} a_i N^i. \quad (2)$$

Here, $Q_{st}$ is the coverage-dependent isosteric heat of adsorption and R is the universal gas constant of 8.3147 J K$^{-1}$mol$^{-1}$. From these results, the Henry's constant ($K_H$) is calculated from where T is temperature.

$$K_H = \exp(-b_0) \cdot \exp(-a_0/T)$$

See Czepirski and Jagiello (1989); Jagiello et al. (1995); Furukawa et al. (2007); and Rahul Banerjee et al. (2009), all of which are incorporated herein by reference.

The Henry's Law selectivity for gas component i over j at 295 K is calculated based on equation:

$$S_{ij} = K_{Hi}/K_{Hj}$$

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

Babarao et al., *Langmuir*, 23:659, 2007.
Bai et al., *Angew. Chem. Int. Ed.*, 47:5344, 2008.
Chen et al., *Acc. Chem. Res.*, DOI:10.1021-2010-00023, 2010.
Chen et al., *Angew. Chem. Int. Ed.*, 44:4745-4749, 2005.
Czepirski and Jagiello, *J. Chem. Eng. Sci.*, 44:797, 1989.

Dinca and Long, *Angew. Chem. Int. Ed.*, 47:6766, 2008.
Eddaoudi et al., *J. Am. Chem. Soc.*, 122:1391, 2000.
Fang et al., *Angew. Chem.* 118:6272, 2006a.
Fang et al., *Chem. Eur. J.*, 12:3754, 2006b.
Furukawa et al., *J. Mater. Chem.*, 17:3197, 2007.
Jagiello et al., *J. Chem. Eng. Data*, 40:1288, 1995.
Kesanli et al., *Angew. Chem., Int. Ed.*, 44:72, 2005.
Lee et al., *Inorg. Chem.*, 48:9971, 2009
Ma and Lin, *Angew. Chem.*, Int. Ed., 48:3637-3640, 2009.
Ma et al., *J. Am. Chem. Soc.*, 129:1858-1859, 2007
Ma et al., *J. Am. Chem. Soc.*, 130:15896-15902, 2008.
Mu et al., *Chem. Commun.*, 2493, 2009.
Myers and Prausnitz, *AIChE J.*, 11:121-127, 1965, 1965.
Rahul Banerjee et al., *J. Am. Chem. Soc.*, 131(11):3875, 2009.
Roquerol et al., In: *Adsorption by Powders and Solids: Principles, Methodology, and Applications*, Academic Press, London, 1999.
Roswell and Yaghi, *J. Am. Chem. Soc.*, 128:304, 2006.
Spek, *J. Appl. Crystallogr.*, 36:7-13, 2003.
Wang et al., *Angew. Chem., Int. Ed.*, 48:5291-5295, 2009.
Xiang et al., *Angew. Chem. Int. Ed.*, 49:4615-4618, 2010.
Xie et al., *Inorg. Chem.*, 49:1158-1165, 2010.
Yang and Zhong, *J. Phys. Chem. B*, 110:17776-17783, 2006.

What is claimed is:

1. A metal-organic framework (MOF) comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid.

2. The MOF of claim 1, further comprising fifteen N,N'-diethylformamide and eight water molecules per repeat unit.

3. The MOF of claim 1, substantially free from any solvent molecules.

4. The MOF of claim 1, having a weight percentage at least 90% attributable to repeat units of the formula $Zn_5(BTA)_6(TDA)_2$.

5. The MOF of claim 1, further comprising one or more than one type of guest molecule.

6. The MOF of claim 5, wherein the guest molecule is a solvent molecule.

7. The MOF of claim 6, wherein the solvent molecule is water.

8. The MOF of claim 6, wherein the solvent molecule N,N'-diethylformamide or N,N'-dimethylformamide.

9. The MOF of claim 5, wherein the guest molecule is a gas molecule.

10. The MOF of claim 9, wherein the gas molecule is $H_2$, $N_2$, Ar, $O_2$, $CO_2$, NO, $NO_2$ or CO.

11. The MOF of claim 9, wherein the guest molecule is an alkane$_{(C1-6)}$, alkene$_{(C2-4)}$, alkyne$_{(C2-6)}$, alcohol$_{(C1-6)}$, arene$_{(C6-8)}$ or a substituted version of any of these.

12. The MOF of claim 11, wherein the alkane$_{(C1-6)}$ is $CH_4$, $C_2H_6$, $C_3H_8$, $C_4H_{10}$, $C_5H_{12}$ or $C_6H_{14}$.

13. The MOF of claim 11, wherein the alkane$_{(C1-6)}$ is a cycloalkane$_{(C3-6)}$ selected from the group consisting of $C_3H_6$, $C_4H_8$, $C_5H_{10}$ and $C_6H_{12}$.

14. The MOF of claim 11, wherein the alkene$_{(C2-6)}$ is $C_2H_4$, $C_3H_6$, $C_4H_8$, $C_5H_{10}$ or $C_6H_{12}$.

15. The MOF of claim 11, wherein the alkyne$_{(C2-6)}$ is $C_2H_2$.

16. The MOF of claim 11, wherein the alcohol$_{(C1-6)}$ is methanol, ethanol, n-propanol, isopropanol, n-butanol or isobutanol.

17. The MOF of claim 11, wherein the guest molecule is an arene$_{(C6-8)}$ or a substituted arene$_{(C6-8)}$.

18. The MOF of claim 17, wherein the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene.

19. A method of storing a compound within a metal-organic framework (MOF) comprising:
   (a) obtaining MOF comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid; and
   (b) combining the MOF with a first compound such that the first compound is stored within the MOF.

20. A method of detecting a compound using an MOF comprising:
   (a) obtaining a MOF comprising a repeat unit of the formula $Zn_5(BTA)_6(TDA)_2$, wherein BTA is the deprotonated anion of 1H-benzo[d][1,2,3]triazole and TDA is the deprotonated dianion of thiophene-2,5-dicarboxylic acid;
   (b) combining the MOF with a first compound such that the first compound enters the MOF to form an MOF•guest complex; and
   (c) comparing the luminescence intensity of the MOF with the luminescence intensity of the MOF•guest complex so as to detect the first compound.

\* \* \* \* \*

UNITED STATES PATENT AND TRADEMARK OFFICE
CERTIFICATE OF CORRECTION

PATENT NO. : 9,127,025 B2  
APPLICATION NO. : 13/589746  
DATED : September 8, 2015  
INVENTOR(S) : Banglin Chen and Shengchang Xiang

Page 1 of 1

It is certified that error appears in the above-identified patent and that said Letters Patent is hereby corrected as shown below:

In the Claims

In claim 8, column 11, line 43, after "molecule" insert --is--.

Signed and Sealed this
Twenty-eighth Day of June, 2016

Michelle K. Lee
*Director of the United States Patent and Trademark Office*